United States Patent [19]

Curtiss, III

[11] Patent Number: 5,888,799
[45] Date of Patent: Mar. 30, 1999

[54] RECOMBINANT AVIRULENT BACTERIAL ANTIGEN DELIVERY SYSTEM

[75] Inventor: Roy Curtiss, III, St. Louis, Mo.

[73] Assignee: Research Corporation Technologies, Inc., Tucson, Ariz.

[21] Appl. No.: 236,941

[22] Filed: May 2, 1994

Related U.S. Application Data

[63] Continuation of Ser. No. 804,277, Dec. 6, 1991, abandoned, which is a continuation of Ser. No. 435,897, Nov. 13, 1989, abandoned, which is a division of Ser. No. 773,894, Sep. 9, 1985, Pat. No. 4,888,170, Continuation-in-part of Ser. No. 314,030, Oct. 22, 1981, abandoned.

[51] Int. Cl.$^6$ .............................. C12N 1/20; C12N 1/00; A61K 39/108; A61K 39/112

[52] U.S. Cl. ................................. 435/252.3; 435/252.3; 435/243; 424/257.1; 424/258.1; 424/184.1

[58] Field of Search ............................... 435/252.3, 69.1, 435/71.1, 252.33, 172.3, 257.3, 252.8; 424/184.1, 252.1

[56] References Cited

U.S. PATENT DOCUMENTS

| | | | |
|---|---|---|---|
| 3,856,935 | 12/1974 | Germanier | 424/92 |
| 4,190,495 | 2/1980 | Curtiss, III | 435/172 |
| 4,550,081 | 10/1985 | Stocker | 435/253 |
| 4,632,830 | 12/1986 | Formal et al. | 424/92 |
| 4,888,270 | 12/1989 | Curtiss, III | 424/93 |

FOREIGN PATENT DOCUMENTS

| | | | |
|---|---|---|---|
| 0080806 | 6/1983 | European Pat. Off. | C12N 15/00 |
| 0080806 | 8/1983 | European Pat. Off. | C12N 15/00 |

OTHER PUBLICATIONS

Clarke Dissertation Abstracts, vol 46: p. 2513 Abstract only.
Jagusztyn–Krynicka et al J. General Microbiology 128: 1135–1145; 1982.
Meadow et al Biochem J. 66: 270–282, 1957.
Curtiss III in Biological Containments The Construction of Safer E. Col. Strains pp. 67–81, 1979.
Curtiss III Miles Int Symp Serio: 45–56 1977, Biological Containment: The Subcordination of E. col K–12 (Recombinant Molecules.
Konicek et al, Folia Microbiol 36: 411–422, 1991.
Dovgan et al, Advances in Veterinary Science and Comparative Medicine 33: 271–300, 1984.
Tijhaar et al, Vaccine 12: 1024–1011, 1994.
Wirth et al.
Meyen et al Cell 30: 45–52, 1982.
Curtiss III Annual Review of Microbiology 50: 507–533 1976.

*Primary Examiner*—James C. Housel
*Assistant Examiner*—S. Devi
*Attorney, Agent, or Firm*—Scully, Scott, Murphy & Presser

[57] ABSTRACT

This invention relates to a vaccine for the immunization of a vertebrate, comprising:

an avirulent derivative of a pathogenic microbe that expresses a recombinant gene derived from a pathogen of said vertebrate it being provided that said avirulent microbe does not normally exchange genetic material with said pathogen, to produce an antigen capable of inducing an immune response in said vertebrate against said pathogen.

8 Claims, 3 Drawing Sheets

RECOMBINANT AVIRULENT BACTERIAL ANTIGEN DELIVERY SYSTEM

This is a continuation of application Ser. No. 804,277, filed on Dec. 6, 1991 which is a Rule 60 Continuation of U.S. Ser. No. 435,897 filed Nov. 13, 1989, now abandoned, which is a Divisional Application of U.S. Ser. No. 773,894 filed Sep. 9, 1985, now U.S. Pat. No. 4,888,170, which is a Continuation-in-Part Application of U.S. Ser. No. 314,030 filed Oct. 22, 1981, now abandoned.

BACKGROUND OF THE INVENTION

The invention described herein was made in the course of work supported by a grant from the Department of Health, Education and Welfare, Public Health Service.

1. Field of the Invention

The present invention relates to vaccines and more particularly to antigenic gene products produced by microbes containing one or more recombinant genes from a pathogenic organism as a vaccine against the pathogenic organism.

2. Description of the Prior Art

Microbial infectious diseases are ubiquitous, although improved public health and the availability of antibiotics have decreased the incidence and minimized the consequences of infectious microbial diseases in the world. In many underdeveloped countries, however, microbial diseases are still rampant. Even in medically advanced countries, bacterial transposons that carry drug-resistance genes and numerous methods for dissemination of drug-resistance plasmids have resulted in drug resistance that has compromised the effectiveness of conventional methods of infectious disease control designed to counteract the effects of infection after infection has occurred. Thus, in the last several years, there has been increased emphasis on the development of vaccines that might prevent, if not eliminate, some infectious diseases.

Since the intact surface of a healthy epidermis is rarely, if ever, penetrated by microbes, the point of initial infection is most often one of the mucous membranes. These include the conjunctiva and the oral, respiratory, gastrointestinal and genitourinary surfaces. The mucous secretions of these membranes as well as the secretions from tear, salivary and mammary glands can contain antibodies against invading pathogens and thus act as a first line of defense against invasive microbes. Enhancing the immune response of the secretory system is thus a desirable goal in inducing immunity against microbial pathogens such as bacteria, viruses, fungi, parasites, etc.

Previously used vaccines against bacterial diseases have generally comprised (I) specific components purified from the etiologic agents, (II) the whole killed etiologic agent, or (III) an avirulent derivative of the etiologic agent as a live vaccine. Numerous vaccines of these three types exist, of which the following are selected examples:

U.S. Pat. No. 4,250,262, discloses methods for recovering the enzyme glucosyltransferase from *Streptococcus mutans* and the use of this purified enzyme in local immunization against dental caries, a Type I vaccine. Details for culturing the bacteria, purifying the enzyme, and using the enzyme to stimulate IgA antibody in saliva are presented for serotype a, c or g of *S. mutans*. Other examples of vaccines from purified specific components of bacteria are found in U.S. Pat. Nos. 4,203,971 and 3,239,749, which disclose a vaccine useful against infection by *Neisseria gonorrhoeae* which consists of a glycoprotein from the outer coat material of gonococci. Injection of the glycoprotein stimulates a bactericidal antibody.

The use of dead *S. mutans* cells to immunize against tooth decay via administering in the mouth, which is disclosed in U.S. Pat. No. 3,931,398, is an example of a Type II vaccine. The inventors recognized that immunoglobulin A (IgA) antibodies were the antibodies being produced and that they resulted in a decrease in plaque formation.

A live bacterial vaccine (Type III) which contains selected strains of *Escherichia coli* bacteria is disclosed in U.S. Pat. No. 3,975,517. The bacteria were treated with dilute formalin to attenuate or partially inactivate them before injection into the mammary gland of a sow. Antibody thereby produced was later found in the milk and protected newborn swine against *E. coli* infections. The formalin treatment that caused the *E. coli* inactivation was only a temporary attenuation of the bacteria and care had to be taken to prevent bacterial recovery before injection. Such recovery would have resulted in serious infection rather than protection.

Another example of a Type III vaccine is described by Germanier et al. in U.S. Pat. No. 3,856,935 wherein a live *S. typhi* Ty21a derivative is employed as an oral vaccine against typhoid infection.

Several problems exist in producing vaccines directly from pathogenic organisms, as indicated in the *E. coli* (Type III) example above. In addition, a principle obstacle to using whole bacteria (living or killed) or impure preparations obtained from the pathogenic bacteria is the presence of antigenic substances in such preparations that may cause undesirable cross reaction. For example, protein antigens produced by *S. mutans* have been reported to cross-react with antigens present in human heart muscle and thus, like other pathogenic bacterial proteins, may pose a problem of safety when used in a vaccine for humans.

Other problems arise in developing a vaccine capable of oral administration, certainly the most desirable form of administration when considered in terms of either widespread use by unskilled administrators in underdeveloped countries or in terms of patient comfort and acceptability. When oral administration is used to stimulate a secretory IgA (sIgA) response, the amount of material that is actually absorbed and capable of stimulating an effective immune response is usually low. The dose of antigen required for oral immunization generally far exceeds that required for systemic induction of humoral immunity (IgG). It is assumed that a large portion of the antigen is degraded by enzymes of the gastrointestinal tract and may be eliminated or absorbed in a nonimmunogenic form.

SUMMARY OF THE INVENTION

Accordingly, it is an object of this invention to provide a vaccine against bacterial infection that does not have antigenic material associated with it that is capable of causing undesirable antibody-antigen reactions in humans or animals.

It is a further object of this invention to provide a vaccine that does not have problems of cross-reactivity to human or animal tissues in a form suitable for oral administration.

It is still a further object of this invention to provide a vaccine that will persist in the mucosal system of humans or animals and thereby stimulate the production of IgA in the secretory system with a concomitant stimulation of the humoral and cellular immune responses.

An additional benefit of the invention is the simultaneous elicitation of secretory, humoral and cellular immune responses.

These and other objects of this invention have been accomplished by providing a vaccine for the immunization of a vertebrate animal comprising a live avirulent derivative of a pathogenic microbe that contains and expresses a recombinant gene of an organism that is a pathogen of said animal.

It is also possible to accomplish the objects of the present invention by providing a vaccine for the immunization of a warm-blooded animal comprising an antigenic gene product of a gene derived from a first organism that is a pathogen of or that produces an allergen of said animal, wherein said gene is expressed in a second organism which produces said gene product and wherein said gene product induces an immune response in said animal when said first organism or said allergen is present in said animal.

BRIEF DESCRIPTION OF THE DRAWINGS

A more complete appreciation of the invention and many of the attendant advantages thereof will be readily obtained as the invention becomes better understood by reference to the following detailed description when considered in connection with the accompanying drawings, wherein.

DETAILED DESCRIPTION OF THE PREFERRED EMBODIMENTS

Figure 1:
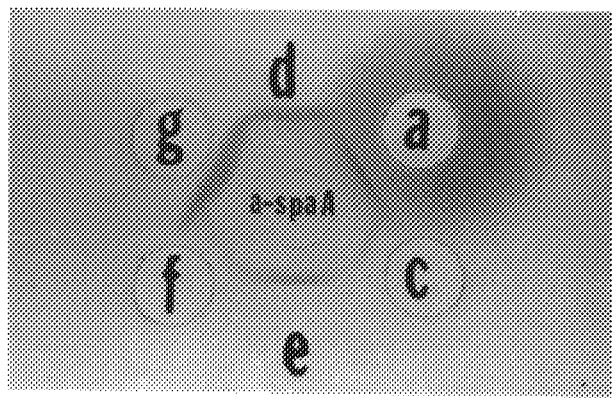
FIG. 1 shows an ouchterlony analysis of reactions between antiserum to purified SpaA protein and concentrated culture supernatant fluids from strains of S. mutans serotypes a, c, e, f, g and d.

Microorganisms prepared by the genetic engineering procedures described herein and suitable pathogenic bacteria from which genes may be obtained are exemplified by cultures now on deposit with the American Type Culture Collection.

Deposit of Strains Useful in Practicing the Invention

Deposits of biologically pure cultures of the following strains were made with the American Type Culture Collection, 10801 University Blvd., Manassas, Va. 20110-2209 on the dates indicated, the accession numbers indicated were assigned after successful viability testing, and the requisite fees were paid. Access to said cultures will be available during pendency of the patent application to one determined by the Commissioner to be entitled thereto under 37 C.F.R. §1.14 and 35 U.S.C. §122. All restriction on availability of said cultures to the public will be irrevocably removed upon the granting of a patent based upon the application and said cultures will remain permanently available for a term of at least five years after the date of the most recent request for furnishing of a sample and in any case for a period of at least 30 years after the date of deposit. Should the cultures become nonviable or be inadvertently destroyed, it will be replaced with a viable culture (s) of the same taxonomic description.

| Strain/Plasmid | | ATCC No. | Deposited |
|---|---|---|---|
| Escherichia coli χ1274 | (pYA619) | 31984 | 10/21/81 |
| Escherichia coli HB101 | (pYA726) | 31985 | 10/21/81 |
| Escherichia coli χ1274 | (pYA601) | 31986 | 10/21/81 |
| Streptococcus mutans | UAB90 | 31987 | 10/21/81 |
| Streptococcus mutans | UAB50 | 31988 | 10/21/81 |
| Streptococcus mutans | UAB308 | 31989 | 10/21/81 |
| Salmonella typhimurium | χ3115 (pYA601/ pYA727) | 39961 | 12/21/84 |
| Salmonella typhimurium | χ3137 (pYA727) | 39962 | 12/21/84 |
| Salmonella typhimurium | χ3245 (pYA601 pYA727) | 39963 | 12/21/84 |
| Salmonella typhi | χ3175 (pYA727) | 39964 | 12/21/84 |

The present inventor has determined that many of the problems associated with previous vaccines against pathogens can be minimized by using avirulent derivatives of pathogenic microbes to produce selected antigens from other pathogens using recombinant DNA techniques, thus providing these antigens in a form essentially free of contaminating antigens from that pathogenic organism. It is preferred to introduce the vaccine directly to the mucous membranes to stimulate secretory IgA production. Recent studies have shown that a central pathway for the antigenic stimulation of IgA precursor cells exists in the gut-associated lymphoid tissues (GALT) and bronchial-associated lymphoid tissues (BALT) and is followed by dissemination of sensitized cells to distant mucosal sites. (Cebra, J. J. et al., Cold Spring Harbor Symp. Quant. Biol. 41: 201–215 (1976). Available data indicate that the salivary, tear and mammary glands and the lamina propria of the gut, respiratory tract, and genitourinary tracts, are supplied by sensitized cells from GALT and BALT. For example, lymphocytes are spread throughout the inner layer of the intestine as isolated cells or small cell clusters. Some of the cell clusters develop into distinct organs, known as lymphoepithelial structures. The principal ones in humans are (1) tonsils (in the pharyngeal wall), (2) the appendix (at the junction of the small and large intestine), and (3) Peyer's patches (oblong lymphoid cell clusters found mostly at the terminal portion of the small intestine). For example, Weisz-Carrington, P. et al., J. Immunol. 123, 1705 (1979) have shown that oral immunization results in the appearance of antibody-producing cells in extra-intestinal lymphoid tissues of mice. Furthermore, in secretory glands, the immunoglobulin class of cells producing anti-ferritin was mostly IgA, while in spleen or peripheral lymph nodes, IgM and IgG ferritin-binding cells were encountered. Thus it is clear that antigenic stimulation of GALT and BALT can lead to a classic immune response whereby B and T cells migrate to secondary lymphoid organs such as spleen and lymph nodes resulting in humoral (antibody) or cellular (T cell) response. It therefore may be assumed that the major natural pathway for stimulation of the immune system occurs through GALT and BALT sensitization. The schematic representation that follows shows pathways of sensitization of B and T lymphocytes, their emigration from GALT and BALT, homing to distant mucosal tissues and differentiation into IgA-producing plasma cells with the eventual modification of the IgA by epithelial cells resulting in the mature secretory IgA molecules.

TABLE I

THE COMMON MUCOSAL IMMUNE SYSTEM

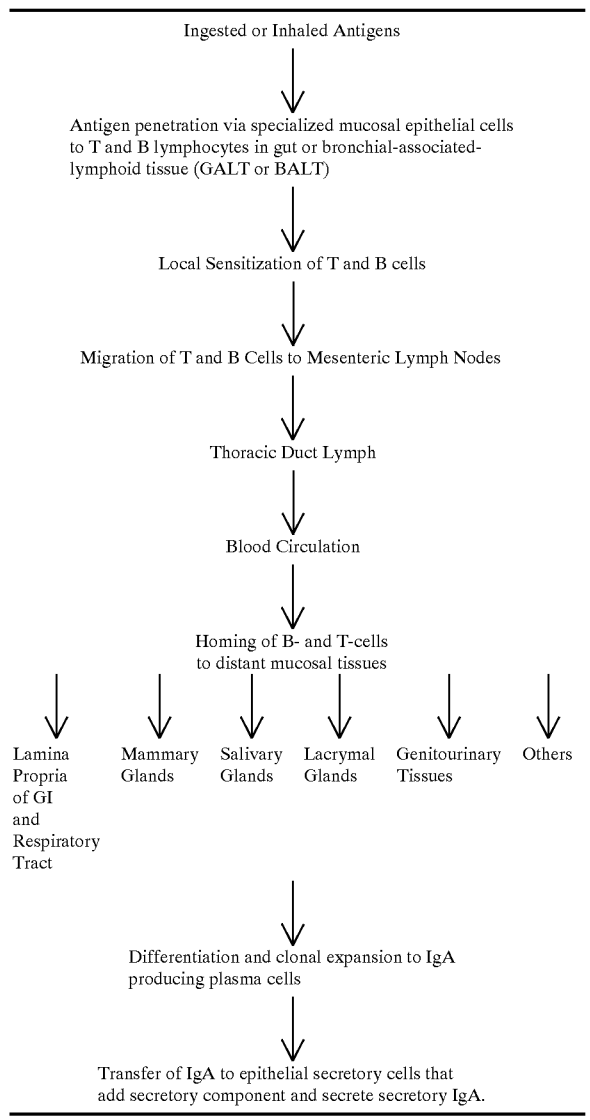

In a preferred embodiment of the invention, the avirulent derivative of a pathogenic microbe also referred to herein as a carrier bacteria can be used to deliver selected antigens to the GALT, for example to the Peyer's patches of the ileum. Some genera of bacteria, such as Salmonella, are known to home to the Peyer's patches (Carter, P. B. and F. M. Collins, *J. Exp. Med.* 139:1189 (1974)). In a well-studied case with *E. coli* RDEC-1, the bacteria specifically attach to, invade or are taken up and persist in the Peyer's patches on the ileum of rabbits, for which this bacterium is species specific (Inman, L. R. and J. R. Cantey, *J. Clin. Invest.* 71:1(1983). Other enteropathogenic *E. coli* strains specific to the human species probably colonize Peyer's patches in mice. *S. typhimurium-E. coli* hybrids have also been shown to colonize Peyer's patches in mice (Hofmann, A. W., et al., *Infect. and Immun.* 22:763 (1978). If these carrier bacteria contain and express a recombinant gene from a pathogenic organism, antibodies against the antigenic gene product produced from the pathogen will be induced. With the advent of recombinant DNA techniques, it now becomes possible to develop totally unique vaccines in which specific antigens are produced, not by the etiologic agent, but by another host strain of bacteria capable of expressing the gene for that antigen. It is also possible, when antigens might cross-react with an antigen of the mammalian host and thus potentiate the induction of autoimmunity, to use recombinant DNA techniques to alter the gene so that the affecting cross-reacting antigenic determinant is not produced. Thus, recombinant DNA techniques can be employed to develop vaccines that do not have any material capable of cross-reacting with vertebrate host antigens or capable of eliciting an autoimmune state.

It is apparent that the present invention has wide applicability to the development of effective vaccines against bacterial, fungal, parasite or viral disease agents where local immunity is important and might be a first line of defense. Some examples are vaccines for the control of pneumonic plague caused by *Yersinia pestis*, of gonorrhea caused by *Neisseria gonorrhoeae*, of syphilis caused by *Treponema pallidum*, and of veneral diseases as well as eye infections caused by *Chlamydia trachomatis*. Species of Streptococci from both group A and group B, such as those species that cause sore throat or heart diseases, *Neisseria meningitidis, Mycoplasma pneumoniae, Hemophilus influenzae, Bordetella pertussis, Mlycobacterium tuberculosis*, and *Mycobacterium leprae* are additional examples of bacteria within the scope of this invention from which genes could be obtained. Viral vaccines, such as those produced against influenza viruses, are also encompassed by this invention. Viral vaccines can also be produced against other viruses, either DNA or RNA viruses, for example from the classes Papovirus, Adenovirus, Herpesvirusl Poxvirus, Parvovirus, Reovirus, Picornavirus, Myxovirus, Paramyxovirus, or Retrovirus. Vaccines to protect against infection by pathogenic fungi, protozoa and parasites are also contemplated by this invention.

In a further embodiment when the immunogenic component of the vaccine is an allergen of the host such a vaccine may be used in an exposure regimen designed to specifically desensitize an allergic host.

In one of its embodiments, the invention can be described as a vaccine for the immunization of a vertebrate animal comprising a live avirulent derivative of a pathogenic microbe that (i) is capable of homing to, attaching to, and invading or being taken up by the GALT and (ii) expresses a recombinant gene derived from an organism that is a pathogen of or that produces an allergen of said animal it being provided that said avirulent microbe does not normally exchange genetic material with said pathogen. Each of the terms in this embodiment of the invention is analyzed in the following discussion.

By vaccine is meant an agent used to stimulate the immune system of a living organism so that protection against future harm is provided. Immunization refers to the process of inducing a continuing high antibody level in an organism, which is directed against a pathogen or antigen to which the organism has been previously exposed. Although the phrase "immune system" can encompass responses of unicellular organisms to the presence of foreign bodies, e.g., interferon production, in this application the phrase is restricted to the anatomical features and mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G, or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example, cellular and humoral immunity. Immune response to antigens is well studied and widely reported. A survey of immunology is given in Davis, Dulbecco et al, Microbiology:. Immunology and Molecular Genetics, Third Edition, Harper and Row, Hagerstown, Md. (1980), the entire of which is herein incorporated by reference.

A vertebrate is any member of the subphylum Vertebrata, a primary division of the phylum Chordata that includes the fishes, amphibians, reptiles, birds, and mammals, all of which are characterized by a segmented bony or cartilaginous spinal column. All vertebrates have a functional immune system and respond to antigens by producing antibodies. Thus all vertebrates are capable of responding to vaccines. Although vaccines are most commonly given to mammals, such as humans or dogs (rabies vaccine), vaccines for commercially raised vertebrates of other classes, such as the fishes and birds if of the nature described herein, are within the scope of the present invention.

One of the essential features of this embodiment of the invention is the use of an avirulent derivative of a pathogenic microbe that homes to the GALT or BALT as a carrier of the gene product which is used for stimulating antibody response against a pathogen or allergen. Avirulent does not mean that a microbe of that genus or species can not ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include viruses, bacteria, protozoa, and unicellular fungi.

It is known that certain species of microbes owing to the similarity of DNA sequences and structure are capable of exchanging genetic information. A convenient listing of species which normally exchange genetic information can be found in the Federal Register for Nov. 23, 1984 (Vol. 49 No. 227, pg 46266 et seq., the contents of which are incorporated herein by reference. Exchanges between the types of microbes listed in appendix A, sublist A, at Page 46274 of the above-cited document, i.e., Escherichia, Shiaella, *Salmonella Enterobacter*, Citrobacter, Klebsiella, Erwinia, *Pseudomonas aeruginosa, Pseudomonas putida, Pseudomonas fluorescens, Serratia marcescens* and *Yersinia enterocolitica* are not within the scope of this invention.

Techniques for transferring genetic material from a first organism to a second organism which normally does not exchange genetic material with the first organism, have recently become widely available as the result of rapidly expanding recombinant DNA technology. In this application, genetic material that has been transferred from one organism into a second, it being provided that the two organisms do not normally exchange genetic material, in such a manner that reproduction of the second organism gives rise to descendents containing the same genetic material is referred to as a recombinant gene. The term gene is being used here in its broadest sense to represent any biological unit of heredity. It is not necessary that the recombinant gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. However, if this gene product is an antigen that will cause formation of antibodies against a similar antigen present in the parent organism, the gene is considered to be within the scope of the term gene as defined in the present invention. Alternatively, if the amino acid sequence of a particular antigen or fragment thereof is known, it is possible to chemically synthesize the fragment or analog thereof by means of automated gene synthesizers or the like and introduce said sequence into the appropriate expression vector. At the other end of the spectrum is a long section of DNA coding for several gene products, one or all of which can be antigenic. Thus a gene as defined and claimed here is any unit of heredity capable of producing an antigen. The gene may be of chromosomal, plasmid, or viral origin.

In order for the gene to be effective in eliciting an immune response, the gene must be expressed. Expression of a gene means that the information inherent in the structure of the gene (the sequence of DNA bases) is transformed into a physical product in the form of a polypeptide, RNA molecule, or other biological molecule by the biochemical mechanisms of the cell in which the gene is located. These may be the cellular mechanisms of an infected cell if the microbe is a virus. The biological molecule so produced is called the gene product. The term gene product as used here refers to any biological product or products produced as a result of the biochemical reactions that occur under the control of a gene. The gene product may be, for example, an RNA molecule, a peptide, or a product produced under the control of an enzyme or other molecule that is the initial product of the gene, i.e., a metabolic product. For example, a gene may first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins, are preferred gene products for use as antigens in vaccines.

In order for a vaccine to be effective in producing antibodies, the antigenic material must be released in such a way that the antibody-producing mechanism of the vaccinated animal can come into play. Therefore the microbe carrier of the gene product must be introduced into the animal. In order to stimulate a preferred response of the BALT and GALT cells as discussed previously, introduction of the microbe or gene product directly into the gut or bronchus is preferred, such as by oral administration, gastric intubation or in the form of aerosols, although other methods of administering the vaccine, such as intravenous, intramuscular or subcutaneous injection or intrapenial or vaginal administration, are possible.

If a live carrier microbe is used, once the carrier microbe is present in the animal, the antigen needs to become available to the animal's immune system. This may be accomplished when the carrier microbe dies so that the antigen molecules are released. However, it is preferred that a gene be selected that controls the production of an antigen that will be made available by the carrier cell to the outside environment without the death of the cell. In this way it is possible to use a viable microbe that will persist in the vaccinated animal, for example in its Peyer's patches, and continue to produce antigen, thereby continually inducing antibody formation. A preferred gene product under these circumstances is a product that is transferred through the cell membrane into the external environment or a product that becomes attached to or embedded in the external membrane so that all or part of the gene product is exposed to the environment. Typical of this latter type of gene product are antigens normally found on the surface of the organism against which protection is desired. If these antigens are transported to the cell surface in a normal manner, antibody formation against the antigens will be greatly enhanced.

However, it is also possible to use a viable carrier incapable of reproduction that dies and releases cytoplasmic and/or perplasmic antigens. When such viable carrier microbes are used, it is possible to employ a wider range of carrier microbes, for example bacteria that would normally be pathogenic, than when viable carriers able to reproduce are used. Of course, the use of "leaky" avirulent mutants that release the contents of the periplasm without lysis is also possible. The use of pathogens to deliver antigens from other pathogens to the GALT or BALT would be inappropriate if it were not for the fact that such pathogens can be rendered avirulent while retaining ability to invade Peyer's patches or the BALT. Alteration of *E. coli* strains to preclude their survival in nature is well-known, and has been described in, for example, U.S. Pat. No. 4,190,495, which is herein incorporated by reference. The same deletion (Δ) mutations (e.g., Δ thyA) used in the laboratory to create bacteria that require a particular nutrient can be used to create avirulent carrier microbes incapable of long-term survival without preventing penetration of Peyer's patches. The Δ asd mutation, which eliminates aspartic acid semialdehyde dehydrogenase (E.C. 1.2.1.11) and thus imposes a requirement for diaminopimelic acid (DAP), would also result in DAP-less death in vivo with release of intracellular and periplasmic proteins. Furthermore, deletion mutations in *S. typhimurium* that prevent aromatic amino acid synthesis result in strains that are avirulent but which can be used to induce effective immunity against subsequent Salmonella infection. This bacterium is described in lioiseth and Stocker, Nature 291, 238 (1981), which is herein incorporated by reference. Such a bacterium provides a convenient source of carrier microbes. A further useful carrier microbe is the Ty21a derivative of *Salmonella typhi* described by Germanier in *J. of Infect. Disease* 131:553 (1975) and in U.S. Pat. No. 3,856,935.

The organism from which the recombinant gene is derived may be any pathogen of the animal being vaccinated or may be an organism that produced an allergen or other antigen of the animal. Allergens are substances that cause allergic reaction, in this case in the animal which will be vaccinated against them. Many different materials may be allergens, such as animal dander and pollen, and the allergic reaction of individual animals will vary for any particular allergen. It is possible to induce tolerance to an allergen in an animal that normally shows an allergic response. The methods of inducing tolerence are well-known and generally comprise administering the allergen to the animal in increasing dosages. Further discussion of tolerence induction is given in the Davis, Dulbecco et al. publication previously cited.

Administration of a live vaccine of the type disclosed above to an animal may be by any known or standard technique. These include oral ingestion, intestinal intubation, or broncho-nasal spraying. All of these methods allow the live vaccine to easily reach the BALT or GALT cells and induce antibody formation and are the preferred methods of administration. Other methods of administration, such as intravenous injection, that allow the carrier microbe to reach the animal's blood stream may be acceptable when the carrier microbe is unable to reproduce. Intravenous and intramuscular injection are also acceptable with other embodiments of the invention using purified antigens, as is described later.

Since preferred methods of administration are oral ingestion, aerosol spray and intestinal intubation, preferred carrier microbes are those that belong to species that home preferentially to any of the lymphoepithelial structures of the intestines of the animal being vaccinated. These strains are preferred to be avirulent derivatives of enteropathogenic strains produced by genetic manipulation of enteropathogenic strains. Strains that home to Peyer's patches and thus directly stimulate production of IgA are most preferred. In animals these include specific strains of *E. coli*, Salmonella, and Salmonella-*E. coli* hybrids that home to the Peyer's patches.

Recombinant DNA techniques are now sufficiently well known and widespread so as to be considered routine. In very general and broad terms, this method consists of transferring the genetic material, or more usually part of the genetic material, of one organism into a second organism so that the transferred genetic material becomes a permanent part of (recombines with) the genetic material of the organisms to which it is transferred. This usually consists of first obtaining a small piece of DNA from the parent organism either from a plasmid or a parent chromosome. A plasmid (also called an extrachromosomal element) is a hereditary unit that is physically separate from the chromosome of the cell. The DNA may be of any size and is often obtained by the action of a restriction endonuclease enzyme which acts to split DNA molecules at specific base- pair sites. The DNA pieces may be transferred into a host cell by various means such as transformation (uptake of naked DNA from the external environment, which can be artificially induced by the presence of various chemical agents, such as calcium ions). Other methods such as transduction are also suitable, wherein the DNA is packaged within a phage such as the so-called cosmid vectors. Once the parent DNA is in the carrier cell, it may continue to exist as a separate piece (generally true of complete transmitted plasmids) or it may insert into the host cell chromosome and be reproduced with the chromosome during cell division.

Although transferring genetic material is relatively straightforward, predicting which transfers will result in expressed genes is not yet possible. This selection process, however, does not present any difficulty to the present invention. Since the host microbe must express the transferred gene and thereby produce an antigen, a "shotgun" approach works well. Antibodies are first produced against the desired antigen, for exanple, fragments of cell membranes from pathogenic microbes, by standard techniques. DNA from the organism that is the source of the antigen is cleaved into multiple fragments by endonucleases, and the fragments are inserted randomly into carrier microbes, preferably by means of cloning vectors. The microbes that express antigens from the pathogen can be easily identified by their reaction with antibody against pathogen antigens. Antigen-expressing microbes can be selected and cloned to give the desired recombinant organism. Shotgun cloning is well known and is described in detail in Maniatis, T., et al., *Molecular Cloning* Cold Spring Harbor Laboratories (1982), which is herein incorporated by reference.

The techniques of gene transfer are not considered to be part of this invention, and any method capable of producing recombinant organisms comprising genes from pathogenic organisms that are expressed in avirulent microbes will suffice. The techniques of DNA isolation, gene cloning, and related techniques are disclosed in great detail in, for example, *Recombinant DNA*, Methods of Enzymology, Volume 68, Ray Wu, ed., Academic Press (1979), which is herein incorporated by reference.

It is also possible in a second and broader embodiment of this invention to provide a vaccine for the immunization of a vertebrate comprising a gene product obtained from a first microbe that expresses a recombinant gene derived from a second organism that is a pathogen of said vertebrate, it being provided that the two organisms do not normally exchange genetic material, wherein said gene product is capable of producing an immune response in said vertebrate against said pathogen.

A gene product so produced will be free of other antigenic material derived from the organism against which immunization or tolerence is being induced. This is of particular importance when dealing with pathogenic organisms known to induce antibodies which react with various cells or organs of the infected animal. For example, some protein antigens produced by *S. mutans* have been reported to cross-react with antigens present in human heart muscle, and thus, like other streptococcal proteins, may pose a particular problem of safety when used in a vaccine for humans. Such problems can be avoided by selected clones of recombinant microbes that produce only antigens that do not exhibit dangerous cross-reactivity.

The principal difference between the two embodiments discussed is that in the first embodiment the living microbes serve as carriers of the antigen while in the second embodiment the vaccine comprises the antigenic gene product in the absence of the living microbes that produce it. Several advantages arise as a result of this second embodiment. Principally, there is no danger of uncontrolled infection by the carrier microbe. Although there was little danger of uncontrolled infection in the first embodiment because of the control available by choice of avirulent strains of microbes and the ability to produce viable strains unable to reproduce, it was nevertheless necessary to use the microbe that produced the antigenic gene product directly as the vaccine. In the second embodiment, it is possible to use any organism into which genes from the pathogen or antigen-producing organism can be introduced to manufacture the gene product essentially in the absence of other antigens capable of harming the vaccinated animal. Thus, an organism that gives a high yield of the desired gene product may be grown and harvested and the gene product may be separated and used as a vaccine without any need for making the organism acceptable for internal administration. A high-yielding non-compatible organism can therefore be used to produce the vaccine.

Any antigenic gene product, for example, those previously discussed, may be produced in accordance with the second embodiment. Shotgun cloning and selection of clones by antibody reaction works equally well for the second embodiment.

Separation of the antigen from other materials present in the second organism remains to be accomplished after clone selection and growth. The separation of specific components from complex mixtures by their physical and chemical properties is well developed. No more than routine experimentation is required for the separation of most antigenic gene products, since the presence of these gene products in any fraction obtained from a mixture can be determined easily by assaying for antibody/antigen reactions. One suitable method of separation that should be applicable to separations of all antigens is the use of an affinity chromotagraphy column comprising an antibody bound to a support material. Such an affinity column should retain the antigen on the column when a crude preparation containing the antigen is passed over the column. Since shotgun cloning and selection of clones by antibody reaction is a preferred method of selecting suitable clones, antibodies will already exist for desired antigens, and preparation of a suitable affinity chromotagraphy column should not be difficult. Other methods of purification, such as ammonium sulfate precipitation and gel filtration, are also suitable.

In summary, the vaccines of this invention are produced by genetic engineering of microbes, comprising two essential steps:

a) selecting a gene coding for an antigen in a pathogenic organism;

b) inserting the gene into an avirulent carrier microbe, wherein the microbe expresses the gene to produce a gene product capable of inducing antibodies against the pathogenic organism or its metabolic products when the gene product (either in the presence or absence of the carrier microbe) is administered to a vertebrate which is to be protected against the pathogenic organism by the vaccine. Steps which take place after these two steps, for example, preparation of the microbe culture for administration or purification of the antigenic gene product are not considered part of the present invention, but are merely routine technical steps in the preparation of the vaccine into its final form. Nevertheless, methods of carrying out the later steps are summarized below.

Vaccines of this invention may contain either the carrier microbe capable of expressing the pathogen-derived gene or may contain the gene product in a cell- and viral-free form. The method of administration is preferably varied to fit the type of vaccine being used. Vaccines containing carrier microbes are preferably administered orally, particularly when colonization of Peyer's patches is desired. Dosage will vary depending on the ability of the carrier microbe to express the recombinant gene and thus produce antigen, but generally will be in concentrations ranging from about $10^2$ to $10^{11}$ microbes preferably from about $10^3$ or $10^4$ to $10^{11}$ microbes and administered ether as a liquid or in enteric-coated capsules. Such preparations are resistant to acid and enzymes in the stomach of the inoculated animal while dissolving in the intestines. Various enteric-coatings are known in the art, for example as disclosed in U.S. Pat. Nos. 3,241,520 and 3,253,944, and are commerically available. A method suitable for preparation of enteric-coated capsules is described in U.S. Pat. No. 4,152,415, which is herein incorporated by reference, and can be easily modified to provide capsules containing the carrier microbes of the present invention. The only required modification is adjustment of the moisture content of the antigen-containing slurry to prevent excessive drying of viable microbes. The amount of drying required is easily determined by routine experimentation.

Cell- and viral-free vaccines containing the pathogen-derived gene product may also be administered orally in enteric-coated capsules as described above or may be administered parenterally (e.g., by intramuscular, subcutaneous, or intravenous injection). The amount required will vary with the antigenicity of the gene product and need only be an amount sufficient to induce an immune response typical of existing vaccines. Routine experimentation will easily establish the required amount. Typical initial dosages of vaccine could be 0.001–1 mg antigen/kg body weight, with increasing amounts or multiple dosages used as needed to provide the desired level of protection.

The pharmaceutical carrier in which the vaccine is suspended or dissolved may be any solvent or solid that is non-toxic to the inoculated animal and compatible with the carrier organism or antigenic gene product. Suitable pharmaceutical carriers include liquid carriers, such as normal saline an other non-toxic salts at or near physiological concentrations, and solid carriers, such as talc or sucrose. Adjuvants, such as Freund's adjuvant, complete or incomplete, may be added to enhance the antigenicity of the gene product if desired. When used for administering via the bronchial tubes, the vaccine is suitably present in the form of an aerosol.

Immunization with a pathogen derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

The above disclosure generally describes the present invention. A more complete understanding can be obtained by reference to the following specific example which is provided herein for purposes of illustration only and is not intended to be limiting unless otherwise specified.

EXAMPLE

DNA molecules from *S. mutans* strains 6715 (serotype g, 45% guanine+cytosine content) and PS14 and GS-5 (serotype c, 35% guanine+cytosine) were cloned into suitable strains of *E. coli* K-12. Shotgun cloning experiments were performed to determine whether *S. mutans* genes were expressed in *E. coli* and, if so, whether they would complement *E. coli* gene defects. The DNA was isolated from the *S. mutans* strains UAB50 (PS14), UAB90, (PS-14), and UAB308 (GS-5) by treating the *S. mutans* cells with the enzyme mutanolysin and then lysing the bacteria with the detergent sodium dodecyl sulfate. The DNA was recovered by ethanol precipitation, restricted with various restriction endonucleases such as EcoRI, HindIII, BamHI, and PstI and used to anneal to pBR322 or pACYC184 vectors cut with the homologous enzyme. Recombinant molecules were formed by the addition of polynucleotide joining enzyme (or DNA ligase) and suitable strains of *E. coli* K-12 such as HB101, χ 1274, and χ 1849 were transformed by the calcium chloride cold shock method. In other experiments, recombinant molecules were formed by ligating DNA to the cosmid vector pJC74, packaging the recombinant molecules by in vitro packaging methodology with components to introduce the recombinant cosmid DNA into suitable strains of *E. coli* K-12 such as HB101 lysogenic for the thermo-inducible lambda prophage χ cI857. Transformant or transductant clones were selected for resistance to an antibiotic for which the cloning vector carried the appropriate drug resistance gene. Tests using a variety of multiple mutant *E. coli* strains indicated that about 40% of the tested *E. coli* gene defects for purine, pyrimidine and amino acid biosynthesis and carbohydrate use could be complemented by *S. mutans* genetic information. The presence of *S. mutans* DNA was verified using Southern blotting analysis. *E. coli* deletion mutants lacking a given function would sometimes grow as rapidly with *S. mutans* genetic information cloned on the multicopy plasmids pBR322 and pACYC184 (available commerically from Bethesda Research Laboratory, Rockville, Md.) as they would if provided with the optimal amount of the required supplement. In general, most *S. mutans* genes were expressed constitutively and were not subject to repression by end products or inducible by appropriate substrates. Gene products of *S. mutans* that are necessary for the transport and phosphorylation of sugars and that probably associate with the cytoplasmic membrane of *S. mutans* function in *E. coli* in much the same way. *S. mutans* gene products that are normally on the cell surface of *S. mutans* or are excreted into the growth medium were is transported across the *E. coli* cytoplasmic membrane and ended up in the periplasmic space. *E. coli* perA mutants that are defective in transport of various periplasmic proteins from the cytoplasm into the periplasm were still able to transport certain *S. mutans* cell surface gene products into the periplasmic space in *E. coli*.

A goal in cloning *S. mutans* genes in *E. coli* was to identify those genes that might contribute to the ability of *S. mutans* to colonize the tooth surface. Glucosyltransferase cleaves sucrose to yield fructose while polymerizing glucose into glucans. *S. mutans* synthesizes both water-soluble glucans which have predominately α 1–6 linkages and water-insoluble glucans which are branched and have α 1–3 linkage in addition to the α 1–6 linkages. A gene for glucosyl-transferase activity from both *S. mutans* PS14 and GS-5 was cloned into *E. coli*. This gene in pYA601 (from PS14) and pYA619 (from GS-5) is contained on a 1730 base pair (bp) DNA fragment which encodes an enzyme that synthesizes water-soluble glucans. This glucosyltransferase, which has a 55,000 molecular weight, is transported into the *E. coli* periplasm without modification. There it is able to cleave sucrose (which can get into *E. coli's* periplasmic space) to liberate fructose which can be used for growth and to synthesize glucans. This work was subsequently reported (Robeson, J. P. et al., *J. Bact.* 152:211–221 (1983). As previously mentioned, immunization with purified glucosyl-tansferase conferred protective immunity against *S. mutans* induced dental caries.

In order to successfully clone various *S. mutans* genes for cell-surface associated proteins that might not have enzymatic activity, an immunological screening procedure was used. In this approach, antibodies were raised against ammonium sulfate precipitated extracellular proteins of *S. mutans* 6715. The pJC74 cosmid cloning system was used and the recombinant molecules were introduced into an *E. coli* strain lysogenic for the χ cI857 thermosensitive prophage. This cloning system is described in Collins et al., *Proc. Nat'l Acad Sci USA*, 75, 4242 (1978), which is herein incorporated by reference. Induction of lysogenic cells in colonies grown at 30° C. by shifting the temperature to 37° caused cell lysis to release any antigens, even if they were localized to the cytoplasm rather than being transported to the exterior surface of E. coli. Using this method and the formation of precipitin bands around the colonies containing antigens cross-reacting with the antibodies against S. mutans extracellular proteins, it was possible to identify numerous clones which expressed S. mutans cell surface associated protein antigens. These clones were given the identifications pYA701 through pYA721. One clone (pYA721) was of particular interest. This clone specifies a 170 k Da protein (the SpaA protein) which was originally encoded by a 5.5 Mdal fragment of S. mutans DNA. This particular protein antigen cross-reacts with protein antigens in all of the serotypes of S. mutans except for serotype b which is a group of S. mutans (correctly known as S. rattus) that principally colonizes rodents and not humans. An Ouchterlony analysis of this cross-reaction is shown in FIG. 1. This work has been subsequently reported (Holt, R. C. et al. Infect. and Immun. 38:147 (1982)).

Figure 2:
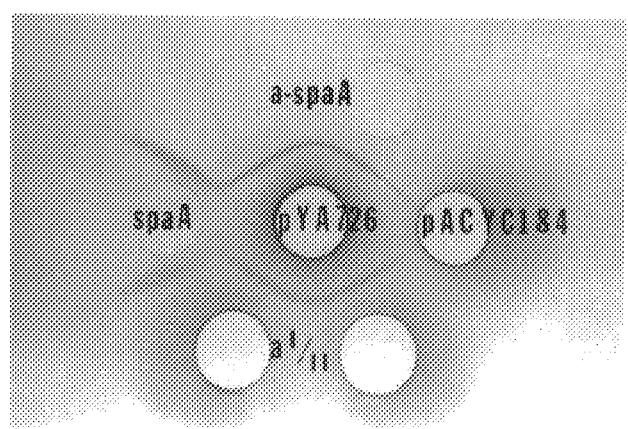
FIG. 2 shows an Ouchterlony analysis of antisera to purified SpaA protein (a SpaA) and S. mutans serotype c antigen I/II (a1/II) with purified SpaA protein, an extract from E. coli χ 1274 (pYA726) which produces SpaA protein and an extract from E. coli χ 1274 which contains the cloning vector (pACYC184)

It should be noted that this 170 k Da protein from serotype g S. mutans is immunologically related to the antigen I/II (FIG. 2) of Russell, M. et al., Infect. and Immun. 28:486 (1980) or the antigen B of Russell, R. R. B., et al. J. Gen'l Micro 114:109 (1979) who also found that injection of this protein purified from the serotype c S. mutans strain Ingbritt into Rhesus monkeys was protective against S. mutans induced dental caries (Russell R. R. B, et al., Immunol, 40, 97 (1980)). SpaA as used herein includes all such cross-reactive antigens.

Immunization of the submandibular region of gnotobiotic rats with killed S. mutans cells induces salivary agglutinins against S. mutans which are in the IgA class. Such immunization was protective against subsequent challenge with virulent S. mutans strains in that mean caries scores were significantly lower in the immunized rats than in the control group that had not been immunized. Subsequent studies demonstrated that ingestion of killed S. mutans cells could likewise stimulate salivary secretory IgA against S. mutans and also confer protective immunity when rats were subsequently challenged with virulent S. mutans strains. (Michalek, S. M. et al., Science 192: 1238–1240 (1976)). These results have been confirmed in human studies in which it was shown that oral ingestion of killed S. mutans resulted in production of sIgA in tears and saliva (Mestecky, J., et al., J. Clin. Invest. 61: 731–737 (1978)). These antibodies were specific against the S. mutans vaccine strain. These studies also indicated a negligible increase in serum agglutinins and gave no evidence of stimulation of any human heart reactive antibodies.

The two S. mutans gene products expressed in E. coli that have been most intensely studied have been the SpaA protein and glucosyltransferase (GTF).

Glucosyltransferase can be assayed by its ability to hydrolyze sucrose to liberate reducing sugars. The Somogyi reagent is used and the reaction is followed at 520 nm. This assay can be used on extracts and on toluenized cells. Enzyme activity in non-denaturing polyacrylamide gels can be measured by soaking the gels in 0.1 sucrose (in 0.2M phosphate buffer, pH 7.0) for 1 to 2 h followed by treating with triphenyl tetrazolium chloride in alkali in the dark to identify the band(s) containing reducing sugar generating activity. It is also possible to assay the GTF for synthesis of glucan using uniformly labelled radioactive sucrose but this is more costly and time consuming. Mono-specific rabbit antibody against GTF produced by E. coli recombinants and monoclonal antibodies can be used for radioimmunoassay (RIA) or Enzyme-linked immunosorbent assays (ELISA) and the antibody tagged with fluorescein or rhodamine isothiocyanate can be used to identify bacterial cells that have GTF on their cell surface.

In terms of purification, GTF is a 55 k protein (FIG. 3) which is soluble in 33% ammonium sulfate. Many E. coli proteins are thus removed from the cell extract by ammonium sulfate precipitation. This is followed by a combination of chromatography on diethylaminoethyl (DEAE) cellulose (DE52); Whatman Ltd.)., Ultrogel AcA54 and Ultrogel AcA44 (LKB) with concentration of pools by ultrafiltration with Amicon membranes to result in a homogeneous GTF preparation. Protein contaminants are less than a few percent since other protein bands are undetectable by either radioactive labelling and radioautography or by Commassie blue straining of SDS polyacrylamide gels. Using this method about 50% GTF recovery can be achieved and some 10 to 15 mg of GTF from a one liter culture of recombinant E. coli cells harboring the pYA601 plasmid have been obtained.

Figure 3:
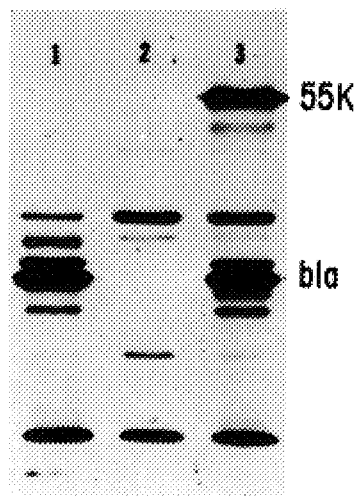
FIG. 3 shows the radiolabelled proteins synthesized in minicells obtained from (1) χ 1849 (pBR322), (2) χ 1849, (3) χ 1849 (pYA601), where the 55 k Da protein is glucosyltransferase A and bla=β-lactamase.
Figure 4:
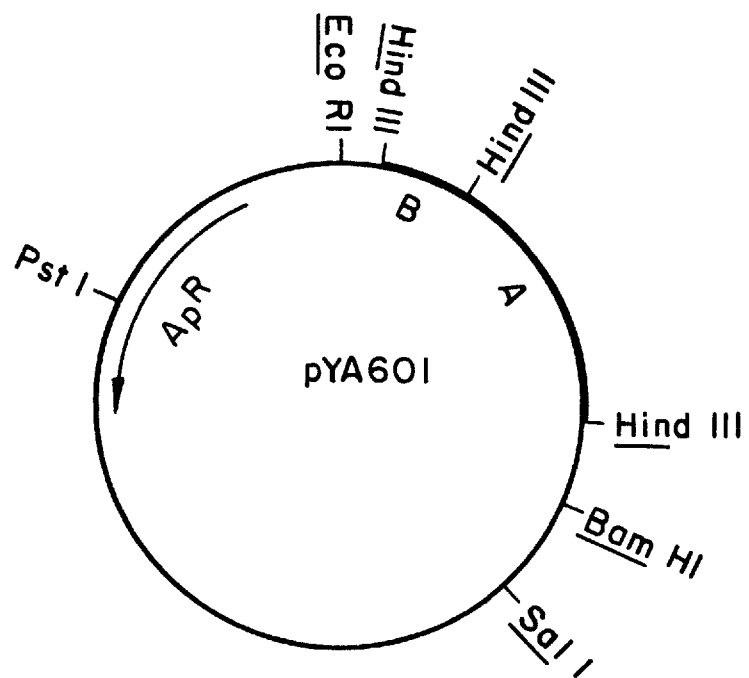
FIG. 4 shows a physical map of pYA601, with the S. mutans DNA insert consisting of two HindIII restriction fragments, A and B, of 1360 and 370 bp in length, respectively.

GTF is synthesized constitutively in E. coli $\chi$ 1849. E. coli cells growing on glucose or raffinose with isopropyl-thio β-galactopyranoside (IPTG) produce about 50% as many glucosyltransferase molecules as β-lactamase molecules which are also encoded on the pBR322 cloning vector (FIG. 3). The gene for glucosyltransferase spans two HindIII fragments of 1360 and 370 bp (FIG. 4). The larger fragment contains the RNA polymerase binding site. (Both fragments have also been cloned within a BamHI fragment in pYA619.) If one subtracts 100 bp for promoter and terminator control sequences, then the two HindIII fragments would specify a protein of only 55 to 58 k in molecular weight.

Because of its size, the SpaA protein can be purified in several steps. When the protein is purified from S. mutans, the cell-free culture supernatant fluid is concentrated to 5% of its original volume by ultrafiltration, sucrose is added to a.concentration of 10% (w/v) and the fraction is incubated at 37° C. for 2 hrs. All glucosyltrans ferase enzymes along with other proteins that bind to dextrans or have affinity for sucrose form complexes that are removed by low speed centrifugation. The supernatant fluid is then run successively on Ultrogel AcA44 and Ultrogel AcA34. Finally, a homogeneous protein is obtained after DEAE cellulose chromatography. In E. coli, the 170 k SpaA protein can be purified from the periplasmic fluid released by cold osmotic shock. Since there are few proteins of this size in the E. coli periplasm, one can obtain homogeneous preparations of this protein by ion exchange chromatography on DEAE cellulose followed by gel filtration chromatography on Ultrogel AcA34.

Figure 5:
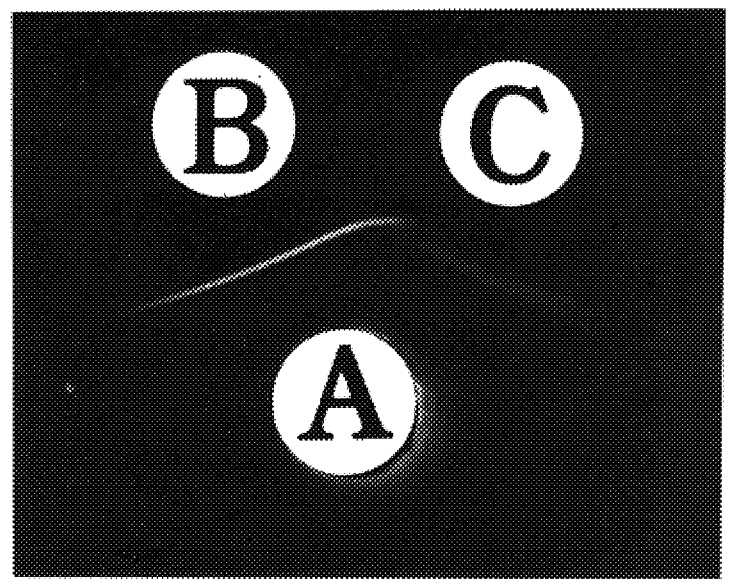
FIG. 5 shows an Ouchterlony analysis of SpaA protein present in the periplasm (B) and cytoplasm (C) of E. coli HB101 (pYA721) where well A contains anti-SpaA serum.

The SpaA protein is assayed immunologically. Monospecific rabbit antibodies against the SpaA protein made by both S. mutans and recombinant E. coli have been made. These antibodies have been used to measure the amount of SpaA protein in the E. coli periplasm (over 80%) vs. the E. coli cytoplasm using both agar double diffusion (FIG. 5) and rocket immunoelectrophoregis. The antibody against the SpaA protein has also been conjugated with rhodamine is isothiocyanate to screen Streptococcal cells for the presence of SpaA protein on their cell surface. This fluorescent antibody can be used to identify E. coli strains expressing the SpaA protein on their cell surface.

Additionally the following recombinant vectors were constructed.

Construction of pYA727 pYA727 possesses the 8.35 kb fragment of *S. mutans* DNA encoding the production of the SpaA protein subcloned from pYA721. This *S. mutans* DNA fragment is contained in the plasmid cloning vector pACYC184, but is an orientation opposite to the orientation of the same 8.35 kb *S. mutans* DNA fragment in the recombinant plasmid pYA726. Both yield comparable levels of SpaA protein. These plasmids are present in either *E. coli* or *S. typhimurium* strains. The pYA727 plasmid seems to be more stable than the pYA726 plasmid when introduced into Salmonella strains.

Construction of Avirulent Derivatives of Pathoqenic Salmonella Strains $\chi$ 3115 and $\chi$ 3137 were derived (see Table II) from the fully virulent *S. typhimurium* strain SR-11 received from Mr. William Benjamin of the Department of Microbiology at the University of Alabama in Birmingham. Transposon mutagenesis using the transposon Tn10 which confers resistance to tetracycline and the generation of deletions of Tn10 and adjacent genetic material during selection of fusaric acid resistance were by the standard methods (R. Davis, D. Botstein, and J. Roth. 1979. Advanced Bacterial Genetics, Cold Spring Harbor Laboratory, Cold Spring Harbor, N.Y.).

$\chi$ 3115 was transformed with pYA601 DNA selecting for ampicillin resistance and then with pYA727 DNA selecting for chloramphenicol resistance. The plasmids pYA601 specifying synthesis of glucosyltransferase A and pYA727 specifying synthesis of the surface protein antigen A, (e.g., SpaA protein) specify different antibiotic resistances and are fully capable of joint replication in the same bacterial cell. This is because the original cloning vectors pBR322 and pACYC184 are compatible; i.e., they are independently replicated in the same bacterial cell.

*S. typhimurium* $\chi$ 3137 was generated in two steps from $\chi$ 3115 (see Table II) so as to introduce an additional mutation providing the deletion of the thyA gene to impose a requirement for thymidine. $\chi$ X3137 was then transformed with pYA727 by selection for chloramphenicol resistance.

$\chi$ 3245 contains the Δ aroA554 mutation described by Hoiseth and Stocker *Nature* 291:238 (1981) as rendering *S. typhimurium* SL1344 avirulent but permitting it to induce protective immunity. $\chi$ 3245 was transformed with pYA601 and pYA727 by selection of ampicillin and chloramphenicol resistance, respectively.

TABLE II

Genetic Properties and Geneology of
Carrier Strains Useful for Practicing the Invention

| | |
|---|---|
| $\chi$3041 | *Salmonella typhimurium* SR-11 |
| ↓ | transduction to TC$^r$ with P22 grown on $\chi$3011 containing Tn10 at the zge locus adjacent to the asd$^+$ gene |
| $\chi$3105 | *S. typhimurium* SR-11 zge::Tn10 |
| ↓ | selection for fusaric acid resistance to result in deletion of Tn10 and adjacent asd gene |
| $\chi$3115 | *S. typhimurium* SR-11ΔasdA3 |
| ↓ | transduction to Tc$^r$ with P22 grown on $\chi$3001 containing Tn10 inserted into the thyA gene |
| $\chi$3134 | *S. typhimurium* SR-11 asdA3 thyA::Tn10 |
| ↓ | selection for fusaric acid resistance to result in deletion of Tn10 and portions of the thyA gene |
| $\chi$3137 | *S. typhimurium* SR-11ΔasdA3ΔthyA42 |
| $\chi$3245 | *S. typhimurium* SL 3261ΔaroA554 hisG46 |
| $\chi$3175 | *S. typhi* Ty21a ga1E |

$\chi$ 1 3175 is *Salmonella typhi* Ty21A. This strain is constructed and described by Rene Germanier (*Journal of Infectious Diseases* 131:553 (1975)) and is described in U.S. Pat. No. 3,856,935. The strain was received from Dr. Louis Baron of the Walter Reed Army Institute of Research, Washington, D.C. It was transformed by the plasmid pYA727 by selection for chloramphenicol resistance.

The Δ asdA3 mutation in $\chi$ 3115 and $\chi$ 3137 fails to revert to Asd$^+$ when over $10^{10}$ bacteria are plated on complete nutrient agar lacking diaminopimelic acid (DAP). Similarly, the Δ thyA42 mutation in $\chi$ 3137 and the Δ aroA554 mutation in $\chi$ 3245 fail to revert when over $10^{10}$ bacteria are plated on minimal agar media lacking thymidine and the aromatic amino acid and vitamins, respectively.

$\chi$ 3115, $\chi$ 3137, $\chi$ 3245, and $\chi$ 3175 all produce substantial quantities of the *S. mutans* SpaA protein. Similarly $\chi$ 3115 and $\chi$ 3245 produce substantial quantities of the *S. mutans*-specified glucosyltransferase A protein. The *S. typhimurium* strains $\chi$ 3115, $\chi$ 3127, and $\chi$ 3245, with or without the plasmids pYA601 and pYA727, are avirulent when introduced into mice, either per orally or by gastric intubation; that is, mice challenged with between $1\times10^7$ and $1\times10^8$ organisms per orally survived, and exhibited no ill effects when fed these quantities of the avirulent derivatives of the fully pathogenic *S. typhimurium* wild-type strains. Control experiments with the fully virulent *S. typhimurium* SR-11 parent strain ($\chi$ 3041) lead to 100% deaths when mice are fed only $1\times10^5$ *S. typhimurium* cells either per orally or by gastric intubation. $\chi$ 3115, $\chi$ 3137, and $\chi$ 3245 with their complements of recombinant plasmids expressing *S. mutans* proteins, are able to localize to the GALT and can be recovered by surgical excision of Peyer's patches. Mice immunized with $\chi$ 3245 possessing the pYA601 and pYA727 plasmids were protected when challenged with fully virulent *S. typhimurium* SR-11 cells several weeks later. In addition, secretory IgA antibodies against both *S. typhimurium* surface antigens and the *S. mutans*-specified SpaA protein encoded in the pYA727 plasmid can be detected in saliva from these immunized mice.

In a related set of confirmatory experiments, nalidixic-acid resistant derivatives of $\chi$ 3115, $\chi$ 3137 and $\chi$ 3245 were tested. The nalidixic acid resistance was conferred by introduction of the gyrA1816 mutation by phage P22 mediated transduction into the respective strains. The function of this marker was simply to permit selective recovery of the Salmonella derivatives after infection, thereby facilitating the analysis of the experiments; the gyrAl1816 marker was not required for the derivatives to perform their role as carrier microbes.

$\chi$ 3115 Nal$^r$, $\chi$ 3137 Nal$^r$, and $\chi$ 3245 Nal$^r$ were administered in several experiments to Balb/c mice by gastric intubation with recovery of organisms in the Peyer's patches (GALT) one hour later. Twenty-four hours later a five-fold increase in titer of these avirulent Salmonella derivatives can be detected in Peyer's patches. In terms of antibody responses, peak titers were obtained in serum of mice against Salmonella antigens and the *S. mutans* gene products on days 15, 8, and 15 after mice were immunized with one dose of $10^9 \chi$ 3115 Nal$^r$, $\chi$ 3137 Nal$^r$, and $\chi$ 3245 Nal$^r$ cells, respectively.

In terms of secretory IgA in saliva, peak titers were detected 22 days after immunization for both Salmonella and *S. mutans* antigens for mice immunized with all three avirulent Salmonella derivatives expressing *S. mutans* surface protein antigens.

Other experiments involved administering the avirulent *S. typhimurium* strains expressing *S. mutans* antigens to mice on three successive days. In these experiments, serum antibody titers against Salmonella and *S. mutans* antigens peaked 30 days after commencement of immunization where secretory IgA antibodies also peaked 30 days after immunization.

The results of these experiments are summarized in Tables III, IV and V below. The serum and secretory antibody titers were determined by ELISA, the wells were coated with sonicates of *S. typhimurium* LT2; *S. mutans* 6715 (serotype g) and *S. mutans* MT8148 (serotype c). As mentioned previously, the spaA gene comes from serotype g and protein antibodies to this protein are cross-reactive with all other serotypes, including serotype c. The gtfA gene, on the other hand, comes from the serotype c strain. Antibodies to GtfA do not react with a comparable gene product from serotype g. The mice were immunized by gastric intubation with $10^9$ organisms either once or three times on successive days.

Comparable studies with the avirulent *S. typhi* Ty21a derivative $\chi$ 3175, expressing synthesis of the *S. mutans* SpaA protein, cannot be performed in mice since *S. typhi* is not a pathogen for mice. This strain can be tested only in human volunteers since *S. typhi* is specific for infection of humans and no other primate species. A large number of studies have been performed, however, with *S. typhi* Ty21a to demonstrate that it is avirulent when fed orally to humans but, yet, induces a protective immunity against subsequent infection with wild-type *Salmonella typhi* isolates.

The invention now being fully described, it will be apparent to one of ordinary skill in the art that many changes and modifications can be made thereto without departing from the spirit or scope of the invention as set forth herein.

TABLE III

SERUM AND SALIVARY ANTIBODY RESPONSE IN BALB/c MICE CHALLENGED with $_\chi$3270 (PYA601/pYA727) = {$_\chi$3245 Nal$^r$ (pYA601/pYA727)}

| Times Challenged | Day Past Challenge | Serum (1/100) | | | Saliva (1/10) | | |
|---|---|---|---|---|---|---|---|
| | | LT2 | 6715 | MT8148 | LT2 | 6715 | MT8148 |
| 1 | 8 | 0.34 | 0.17 | 0.82 | <0.1 | <0.1 | <0.1 |
| | | 0.14 | 0.15 | 0.65 | <0.1 | <0.1 | <0.1 |
| | 15 | 0.93 | 0.28 | 1.56 | <0.1 | <0.1 | <0.1 |
| | | 1.09 | 1.20 | 2.18 | 0.11 | <0.1 | <0.1 |
| | 22 | 0.60 | 0.14 | 0.80 | 0.22 | 0.15 | 0.13 |
| | | 0.38 | 0.16 | 0.96 | 0.16 | 0.11 | <0.1 |
| 3 | 16 | 1.03 | 0.18 | 0.66 | 0.19 | 0.15 | <0.1 |
| | | 2.04 | 0.19 | 0.71 | 0.17 | 0.11 | <0.1 |
| | 23 | 1.31 | 0.18 | 1.01 | 0.14 | 0.16 | 0.32 |
| | | 1.05 | 0.15 | 0.98 | 0.21 | 0.12 | 0.28 |
| | 30 | 1.56 | 0.17 | 0.99 | 1.05 | 0.35 | 0.87 |
| | | 1.98 | 0.19 | 1.22 | 0.97 | 0.41 | 0.93 |

TABLE IV

SERUM AND SALIVARY ANTIBODY REPSONSE IN BALB/c MICE CHALLENGED WITH $_\chi$3267 (pYA727 (spaA) = ($_\chi$3137 Nal$^r$ (pYA727)}

| Times Challenged | Day Past Challenge | Anti Ig Serum (1/100) | | | IgA Saliva (1/10) | | |
|---|---|---|---|---|---|---|---|
| | | LT2 | 6715 | MT8148 | LT2 | 6715 | MT8148 |
| 1 | 8 | 1.11 | 0.26 | 0.41 | <0.1 | <0.1 | <0.1 |
| | | 0.93 | 0.19 | 0.21 | 0.23 | <0.1 | <0.1 |
| | 15 | 0.61 | 0.21 | 0.44 | 0.21 | <0.1 | <0.1 |
| | | 0.21 | 0.17 | 0.49 | <0.1 | <0.1 | <0.1 |
| | 22 | 0.15 | 0.17 | 0.29 | 2.05 | 0.45 | 1.10 |
| | | 0.20 | 0.28 | 0.42 | 0.21 | 0.16 | 0.15 |
| 3 | 16 | 0.46 | 0.12 | 0.32 | 0.13 | <0.1 | 0.11 |
| | | 0.19 | 0.20 | 0.21 | 0.12 | <0.1 | <0.1 |
| | 23 | 0.35 | 0.20 | 0.41 | 0.13. | <0.1 | <0.1 |
| | | 0.31 | 0.15 | 0.39 | 0.12 | <0.1 | <0.1 |
| | 30 | 2.05 | 0.16 | 0.65 | 0.65 | 0.32 | 0.58 |
| | | 1.56 | 0.19 | 0.70 | 0.76 | 0.18 | 0.72 |

TABLE V

SERUM AND SALIVARY ANTIBODY RESPONSE
IN BALB/c MICE CHALLENGED
WITH $_\chi$3266 (pYA727 (gtfA)/pYA727 (spaA)) =
($_\chi$3115 Nal$^r$ (pYA601)/pYA727)}

| Times Challenged | Day Past Challenge | Serum (1/100) | | | Saliva (1/10) | | |
|---|---|---|---|---|---|---|---|
| | | LT2 | 6715 | MT8148 | LT2 | 6715 | MT8148 |
| 1 | 8 | 0.25 | 0.12 | 0.80 | <0.1 | <0.1 | 0.12 |
| | | 0.29 | 0.13 | 1.85 | <0.1 | <0.1 | 0.09 |
| | 15 | 1.66 | 0.20 | 2.14 | <0.1 | <0.1 | <0.1 |
| | | 0.65 | 0.45 | 0.95 | <0.1 | <0.1 | <0.1 |
| | 22 | 0.79 | 0.48 | 1.15 | 0.13 | <0.1 | <0.1 |
| | | 2.18 | 0.39 | 1.22 | 0.12 | <0.1 | <0.1 |
| 3 | 16 | 0.68 | 0.11 | 0.57 | 0.12 | <0.1 | <0.1 |
| | | 0.34 | 0.11 | 0.58 | 0.15 | 0.15 | <0.1 |
| | 23 | 0.58 | 0.14 | 0.98 | 0.35 | <0.1 | <0.1 |
| | | | | | 0.64 | 0.10 | <0.1 |
| | 30 | 0.87 | 0.24 | 0.98 | 0.22 | 0.19 | 0.21 |
| | | 0.92 | 0.51 | 1.32 | 0.75 | 0.45 | 0.81 |

What is claimed as new and desired to be secured by Letters Patent of the United States is:

1. An antigenic preparation comprising an avirulent derivative of a pathogenic bacterial species which expresses a product of a nucleic acid sequence coding for an antigen of a pathoaenic organism or infectious disease agent of a vertebrate host, wherein said product of said nucleic acid sequence coding for said antigen of said pathogenic organism or infectious disease agent does not possess a cross reacting antigenic determinant with said vertebrate host and wherein said avirulent derivative and said pathogenic organism or infectious disease agent do not normally exchange genetic information, thereby requiring use of recombinant DNA cloning to achieve expression of said product of said nucleic acid sequence in said avirulent derivative and wherein said antigenic preparation homes to lymphoid tissue or a lymphoepithelial structure of said vertebrate host and induces an immune response in said vertebrate host upon administration thereto.

2. A method of inducing an immune response in a vertebrate host which comprises administering to said vertebrate host an antigenic preparation comprising an avirulent derivative of a pathogenic bacterial species which expresses a product of a nucleic acid coding for an antigen of a pathogenic organism or infectious disease agent of a vertebrate host, wherein said product of said nucleic acid sequence coding for said antigen of said pathogenic organism or infectious disease agent does not possess a cross reacting antigenic determinant with said vertebrate host and wherein said avirulent derivative and said pathogenic organism or infectious disease agent do not normally exchange genetic information, thereby requiring use of recombinant DNA cloning to achieve expression of said product of said nucleic acid sequence in said avirulent derivative and wherein said antigenic preparation homes to lymphoid tissue or a lymphoepithelial structure of said vertebrate host and induces an immune response in said vertebrate host upon administration thereto.

3. A method of making an antigenic preparation which comprises transforming an avirulent derivative of a pathogenic bacterial species with a nucleic acid sequence coding for an antigen of a pathogenic organism or infectious disease agent of a vertebrate host wherein said product of said nucleic acid sequence coding for said antigen of said pathogenic organism or infectious disease agent does not possess a cross reacting antigenic determinant with said vertebrate host and wherein said avirulent derivative and said pathogenic organism or infectious disease agent do not normally exchange genetic information thereby requiring use of recombinant DNA cloning to achieve expression of said product of said nucleic acid sequence in said avirulent derivative and wherein said antigenic preparation homes to lymphoid tissue or a lymphoepithelial structure of said vertebrate host and induces an immune response in said vertebrate host upon administration thereto.

4. A recombinant avirulent derivative of a pathogenic bacterial species which expresses a product of a nucleic acid sequence coding for an antigen of a pathogenic organism or infectious disease agent of a vertebrate host, wherein said product of said nucleic acid sequence coding for said antigen of said pathogenic organism or infectious disease agent does not possess a Cross reacting antigenic determinate with said vertebrate host and wherein said avirulent derivative and said pathogenic organism or infectious disease agent do not normally exchange genetic information, thereby requiring use of recombinant DNA cloning to achieve expression of said product of said nucleic acid sequence in said avirulent derivative and wherein said recombinant avirulent derivative of a pathogenic bacterial species homes to lymphoid tissue or a lymphoepithelial structure of said vertebrate host and induces an immune response in said vertebrate host upon administration thereto.

5. An antigenic preparation according to claim 1 wherein said avirulent derivative of a pathogenic bacterial species is selected from the group consisting of Salmonella, E. coli, and Salmonella-E. coli hybrids.

6. A method of inducing an immune response in a vertebrate host according to claim 2 wherein said avirulent derivative of a pathogenic bacterial species is selected from the group consisting of Salmonella, E. coli, and Salmonella-E. coli hybrids.

7. A method of making an antigenic preparation according to claim 3 wherein said avirulent derivative of a pathogenic bacterial species is selected from the group consisting of Salmonella, E. coli, and Salmonella-E. coli hybrids.

8. A recombinant avirulent derivative of a pathogenic bacterial species according to claim 4 wherein said pathogenic bacterial species is selected from the group consisting of Salmonella, E. coli, and Salmonella-E. coli hybrids.

* * * * *

UNITED STATES PATENT AND TRADEMARK OFFICE
CERTIFICATE OF CORRECTION

PATENT NO. : 5,888,799
DATED : March 30, 1999
INVENTOR(S) : Roy Curtiss III

It is certified that error appears in the above-identified patent and that said Letters Patent is hereby corrected as shown below:

Title page:
Section [21]: "236,941" should read -- 08/236,941 --
"OTHER PUBLICATIONS", Line 8 "E. Col."should read -- E. Coli --."

Column 7:
Line 54: "Shiaella" should read -- Shigella --

Column 16:
Line 39: "a.concentatration" should read -- a concentration --
Line 60: "immunoelectrophoregis" should read -- immunoelectrophoresis --

Column 17:
Line 13: "Pathoqenic" should read -- Pathogenic --

Column 20, table IV:
Line 61: "0.61" should read -- 0.81 --
Line 66: "0.13" should read -- 0.13 --

Column 21, table V:
Line 3: "(pYA727' should read -- (pYA601 --

Signed and Sealed this

Fourth Day of September, 2001

Attest:

NICHOLAS P. GODICI
Attesting Officer
Acting Director of the United States Patent and Trademark Office